United States Patent [19]

Vegoe et al.

[11] Patent Number: 5,180,372
[45] Date of Patent: Jan. 19, 1993

[54] SPLITTABLE CATHETER AND METHOD

[75] Inventors: Brett R. Vegoe, Mound; Richard L. Molacek, Maple Grove, both of Minn.

[73] Assignee: Medtronic, Inc., Minneapolis, Minn.

[21] Appl. No.: 763,788

[22] Filed: Sep. 23, 1991

[51] Int. Cl.⁵ .............................................. A61M 5/18
[52] U.S. Cl. .................................................. 604/161
[58] Field of Search ................ 604/158, 161, 280, 264

[56] References Cited

U.S. PATENT DOCUMENTS 4,411,654  10/1983  Boarini et al. .
4,776,846  10/1988  Wells ................................... 604/161
4,883,468  11/1989  Kousai et al. ....................... 604/161
4,921,882   5/1990  Senich .
4,983,168   1/1991  Moorehead .......................... 604/161

Primary Examiner—Gene Mancene
Assistant Examiner—Michael Lynch
Attorney, Agent, or Firm—Daniel W. Latham; Harold R. Patton

[57] ABSTRACT

An improved placement catheter of the type having a longitudinal line of weakness whereby the catheter may be split longitudinally. The improved catheter is made with radiation cross-linked tubing to provide better splittability.

6 Claims, 1 Drawing Sheet

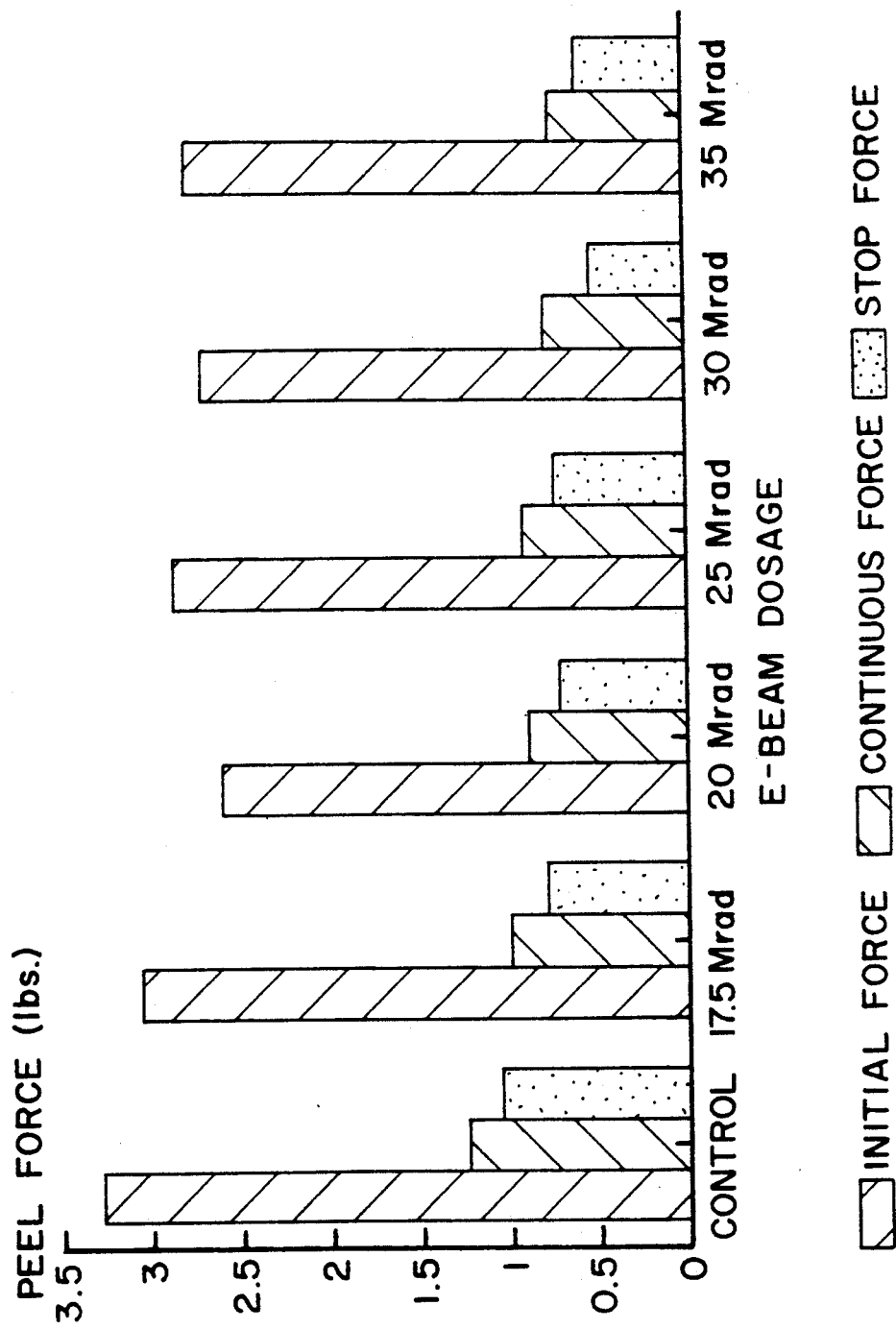

SPLITTABLE CATHETER AND METHOD

BACKGROUND OF THE INVENTION

This invention relates to splittable catheters used in procedures for inserting catheters or pacing leads into a human body. A hollow needle that has a coaxial splittable placement catheter thereon is used to penetrate the vein. The needle is then removed, leaving the placement catheter extending through the penetration and into the vein. A catheter, guidewire or pacing lead is then inserted into the vein through the lumen of the placement catheter. The placement catheter is designed to split longitudinally so that it can be removed from the vein without removing the inserted device.

A variety of methods have been used to impart splittability to the placement catheter. For example, in U.S. Pat. No. 4,411,654 issued to Boarini et al, longitudinal lumens or grooves are placed 180 degrees apart into the wall of the catheter during extrusion to provide lines of weakness from the proximal end to the distal end of the catheter along which the catheter will rupture if it is peeled away from an inserted device. A similar effect may be achieved by using a tool to longitudinally score the wall of the catheter after it is molded or extruded. While these methods are generally effective, the lines of weakness provided may be inadequate to provide smooth splittability for the catheter, causing the catheter to tear off of the lines of weakness. Also, if the lines of weakness provided weaken the catheter excessively, it could cause an unexpected rupture of the catheter during the insertion procedure.

It is therefore an object of the present invention to provide a placement catheter that requires reduced force to split the catheter while maintaining the catheter's strength.

It is also an object of the present invention to provide a placement catheter which splits smoothly along lines of weakness in the catheter while minimizing tears off the lines of weakness.

SUMMARY OF THE INVENTION

These and other objects have been achieved in the present invention. We have found an improvement for a placement catheter made from polymeric tubing which has been provided with a longitudinal line of weakness extending from a proximal end to a distal end of the catheter. The improvement is to use a radiation cross-linked tubing as the polymeric tubing material. The tubing is preferably treated after it is extruded by the application of radiation in a type and amount sufficient to cause cross linking of the polymeric material of the tube.

BRIEF DESCRIPTION OF THE DRAWINGS

FIG. 1 is a graph showing the peel force required to split a placement catheter according to the prior art and also for placement catheters made by the application of electron beam radiation according to the present invention.

DETAILED DESCRIPTION OF THE INVENTION

The present invention is an improvement for a placement catheter made from polymeric tubing which has been provided with a longitudinal line of weakness extending from a proximal end to a distal end of the catheter. The improvement is to use a radiation cross-linked tubing as the polymeric tubing. The tubing is preferably treated after it is extruded by the application of radiation of a type and amount sufficient to cause cross-linking of the polymeric material of the tube.

The polymer used for the tubing can be any polymer or polymer blend suitable for use in placement catheters that can be cross-linked by the application of radiation. For example, polyethylene, polypropylene, polyurethane, polyvinylchloride, ethylene copolymers or fluoro-polymers could be used. A preferred polymer is low density polyethylene or linear low density polyethylene or mixtures thereof.

The radiation source can be any radiation source that will effect cross-linking of the polymeric material of the catheter tube. For example, electrons, gamma rays, X-rays, beta rays or ultraviolet light could be used depending on the polymeric material of the tube. In a preferred embodiment employing low density polyethylene polymers, an electron-beam source is preferred. Equipment for producing electron-beams suitable for treating tubing according to the present invention can be obtained commercially. For example, a system from Energy Sciences Inc., Bedford, Mass. could be used.

The amount of radiation required for the present invention depends on the polymeric material used for the tubing and can be easily determined experimentally for each material. Generally, the desired radiation dosage is that which will reduce the force required to peel the placement catheter apart without causing such degradation of the material that the material will tear off of the provided lines of weakness. The point at which degradation starts for the material may be determined by plotting the 100% secant modulus of the material against the radiation dosage. When the modulus drops, degradation of the material and splitting off of the lines of weakness can be expected. In a preferred embodiment in which a 50/50 blend of low density polyethylene/linear low density polyethylene was used in tubing with a diameter of 0.187 inches and a wall thickness of 0.026 inches was irradiated with an electron beam, a radiation dose at about 22.5 Mrad or below was found to produce acceptable results.

A further disclosure of the present invention will be presented in the following illustrative examples.

EXAMPLE 1

Lead introducer tube samples made from a 50/50 blend of low density polyethylene/linear low density polyethylene were tested for splittability following radiation treatments of varying intensity. The tubing had a diameter of 0.87 inches and a wall thickness of 0.026 inches and was provided with longitudinal, opposing scores to provide longitudinal lines of weakness by which it could be peeled apart. The test samples were sent to Retroperfusion Systems, Inc., Irvine, California for irradiation at various dosages. The irradiated samples were then tested for peel force values according to three test protocols identified in FIG. 1 as "initial force", "continuous force" and "start-stop force". "Initial force" was measured as the force in pounds required to start the split in the placement catheter. "Continuous force" was measured as the highest force in pounds recorded during the entire splitting of the placement catheter excluding the initial force. "Start-stop force" was measured as the force in pounds required to restart the splitting action after stopping. The results of those tests are given in FIG. 1.

EXAMPLE 2

Lead introducer tube samples as set forth in Example 1 were sent to E-Beam Services, Plainview, New York for electron beam irradiation at various dosage levels. The samples were tested for parameters including ultimate tensile strength, elongation at break and 10% secant modulus. The mean results for those test parameters are given in Table 1.

TABLE 1

| Dosage Level (Mrad) | Ultimate Tensile (psi) | Elongation (percent) | Secant Modulus (psi) |
| --- | --- | --- | --- |
| none | 3922 | 2768 | 1428 |
| 15 | 4213 | 2159 | 1439 |
| 20 | 4047 | 1938 | 1463 |
| 22.5 | 3857 | 1714 | 1525 |
| 25 | 3793 | 1598 | 1502 |
| 27.5 | 3771 | 1561 | 1504 |
| 30 | 3494 | 1391 | 1513 |
| 32.5 | 3807 | 1462 | 1533 |

With respect to these samples, ease of splittability was noted to be better with increasing dosage level but that some samples at 25 Mrad and above tended to tear off of the score lines.

While the invention has been described above in connection with particular embodiments, one skilled in the art will appreciate that the invention is not necessarily so limited and that numerous other embodiments, examples, uses and modifications of and departures from the embodiments, examples and uses may be made without departing from the inventive concepts.

We claim:

1. In a method of making a placement catheter by providing polymeric tubing with a longitudinal line of weakness extending from a proximal end to a distal end of the catheter, the improvement comprising: applying cross-linking radiation to the weakened tubing.

2. The method of claim 1 wherein the polymeric tubing comprises a polymer or polymer blend selected from the group consisting of polyethylene, polypropylene, polyurethane, polyvinylchloride, ethylene copolymers and fluoropolymers.

3. The method of claim 1 or 2 wherein the radiation applied to the polymeric tubing is from a radiation source selected from the group consisting of electron-beam, gamma rays, and ultraviolet light.

4. The method of claims 1 or 2 wherein the tubing is extruded.

5. The method of claim 2 wherein the polymeric tubing is made from linear low density polyethylene.

6. The method of claim 3 wherein the radiation applied to the polymeric tubing is less than about 22.5 Mrad.

* * * * *

UNITED STATES PATENT AND TRADEMARK OFFICE
CERTIFICATE OF CORRECTION

PATENT NO. : 5,180,372

DATED : January 19, 1993

INVENTOR(S) : Brett R. Vegoe and Richard L. Molacek

It is certified that error appears in the above-indentified patent and that said Letters Patent is hereby corrected as shown below:

Column 3, line 7, "10%" should be --100%--.

Signed and Sealed this

Sixteenth Day of August, 1994

Attest:

BRUCE LEHMAN

Attesting Officer     Commissioner of Patents and Trademarks